United States Patent
Klabunde et al.

(12)

(10) Patent No.: US 7,411,491 B2
(45) Date of Patent: Aug. 12, 2008

(54) METHOD OF CONTROLLING WIRELESS DATA TRANSMISSION BY SWITCHING BETWEEN SHORT-RANGE AND LONG-RANGE RADIO TECHNOLOGIES

(75) Inventors: Karin Klabunde, Bochum (DE); Guido Muesch, Linnich (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 108 days.

(21) Appl. No.: 10/559,317

(22) PCT Filed: May 27, 2004

(86) PCT No.: PCT/IB2004/050785

§ 371 (c)(1),
(2), (4) Date: Apr. 12, 2006

(87) PCT Pub. No.: WO2004/109992

PCT Pub. Date: Dec. 16, 2004

(65) Prior Publication Data

US 2007/0010256 A1 Jan. 11, 2007

(30) Foreign Application Priority Data

Jun. 6, 2003 (EP) .................................. 03101659

(51) Int. Cl.
*G08B 1/08* (2006.01)
(52) U.S. Cl. .............................. 340/539.12; 340/539.1; 340/539.11
(58) Field of Classification Search ............... 340/539.1, 340/539.12, 539.11, 539.13
See application file for complete search history.

(56) References Cited

U.S. PATENT DOCUMENTS

| 5,657,317 | A | 8/1997 | Mahany et al. ............... 370/338 |
| 5,903,548 | A | 5/1999 | Delamater .................... 370/310 |
| 6,400,946 | B1 | 6/2002 | Vazvan et al. ................ 455/432 |
| 7,020,701 | B1 * | 3/2006 | Gelvin et al. ................ 709/224 |
| 7,155,202 | B2 * | 12/2006 | Helal ....................... 455/404.1 |
| 7,155,290 | B2 * | 12/2006 | Von Arx et al. ................ 607/60 |
| 2002/0029258 | A1 | 3/2002 | Mousseau et al. ........... 709/218 |
| 2002/0093956 | A1 | 7/2002 | Gurin ......................... 370/389 |

FOREIGN PATENT DOCUMENTS

WO    WO 01/22662 A1    3/2001
WO    WO 01/67684 A2    9/2001

OTHER PUBLICATIONS

Berggren, M.; Wireless Communication in Telemedicine Using Bluetooth and IEEE 802. 11b; 2001 ; Dept. of IT-Uppsala U.; report 2001-028; pp. 1-32.
Hura, A.M.; Bluetooth-Enabled Teleradiology: Applications and Complications; 2002; J. of Digital Imaging; 15(1)221-223.

* cited by examiner

*Primary Examiner*—Daryl C Pope

(57) ABSTRACT

The invention relates to a device, in particular a patient monitoring system with a mobile terminal unit (1) for acquiring patient data. The measured data is transferred from the terminal unit (1) via a short-range radio technology (2) (e.g. Bluetooth) to a data monitor (3) arranged at the patient's bedside when the patient is in the vicinity thereof. If necessary, communication can be switched to a long-range radio technology (7) (e.g. WLAN) to ensure interruption-free data transmission while the patient moves around.

11 Claims, 1 Drawing Sheet

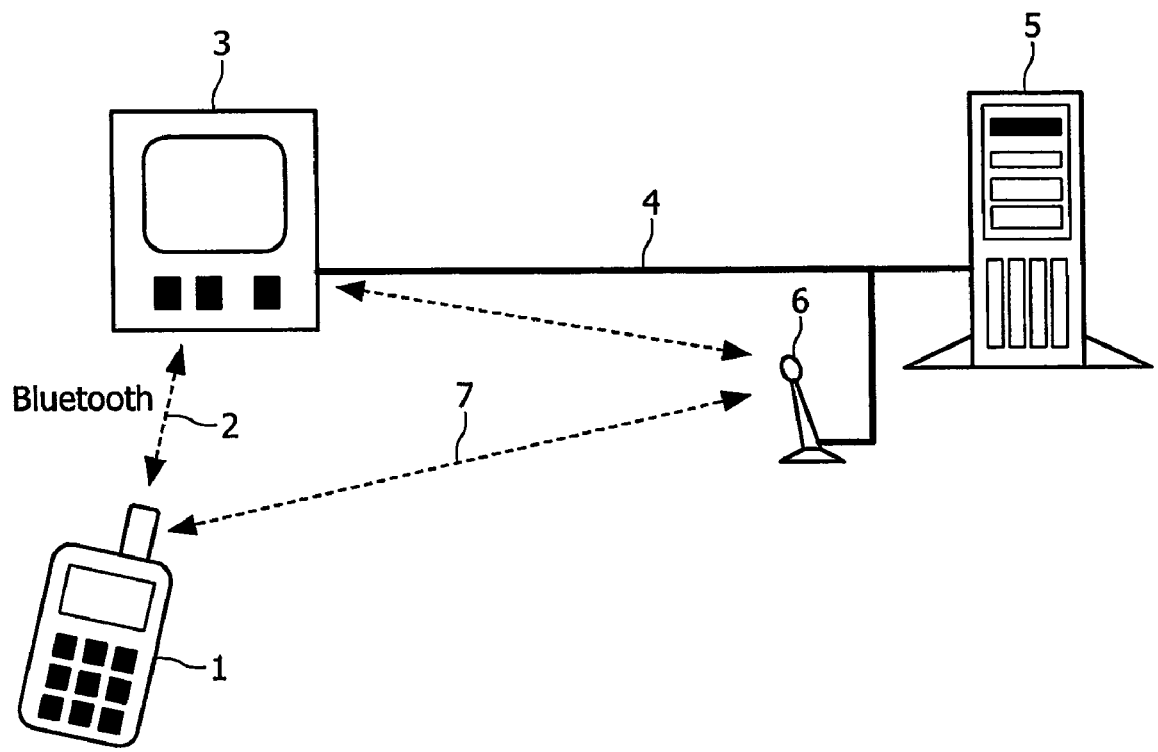

METHOD OF CONTROLLING WIRELESS DATA TRANSMISSION BY SWITCHING BETWEEN SHORT-RANGE AND LONG-RANGE RADIO TECHNOLOGIES

The invention relates to a method of controlling wireless data transmission from a mobile terminal unit to a receiving system. It also relates to a patient monitoring system employing said method for mobile acquisition of physiological parameters from a patient.

In patient monitoring systems, one or more physiological parameters such as a patient's electrocardiogram (ECG) are continuously monitored. The patient carries a mobile terminal unit on his body, which is provided with appropriate sensors to acquire the desired data. If the patient stays in bed and is stationary, in known systems the terminal unit is connected via a cable to the data monitor next to the patient's bed. The data monitor redirects the data transmitted by the terminal unit to a central station to which it is connected via a wireless local area network (WLAN). If the patient wishes to move around freely, the wire-bound link to the data monitor must be released and data transfer must be handed over to wireless radio technology. A disadvantage is then that the patient has to rely on the assistance and input of medical personnel to switch between stationary and mobile data acquisition.

Within the context of the non-continuous data transmission from a central processor to a mobile terminal unit, United States patent application US-2002 0 029 258 discloses that the central processor determines the current location of the mobile terminal unit and selects an optimal transmission route via short-range or long-range radio technology. In the light of the foregoing, it is an object of the invention to provide a means for controlling data transmission from a mobile terminal unit to a receiving system which, particularly when used in a patient monitoring system, enables comfortable data acquisition.

This object is achieved by dint of a method with the features of claim 1 and by dint of a patient monitoring system with the features of claim 8. Advantageous implementations are defined in the dependent claims.

The method according to the invention serves to control wireless data transmission from a mobile terminal unit to a receiving system. It comprises the following steps or features:

The terminal unit can be operated in a first mode in which it transmits the desired data to the receiving system via short-range radio technology. If the quality of said short-range radio technology falls below a first predetermined threshold, the operation switches to a second mode.

In said second mode, the terminal unit transmits the desired data via a long-range radio technology to the receiving system. However, as soon as the quality of the short-range radio technology rises above a second predetermined threshold, the operation switches to the first mode. In particular, the second threshold can be identical to the first threshold mentioned in a). However, it can be higher than the first threshold, in order to avoid unwanted oscillation between the radio technologies through hysteresis. In order to be able to compare the quality of the short-range radio technology with the (second) threshold during communication via the long-range radio technology, the mobile terminal unit seeks, preferably at given intervals, to build a communication link via the short-range radio technology.

With the switch taking place under a) or b) between the two available modes or radio technologies, the communication link via the previous radio technology is maintained until the link is fully established via the subsequent radio technology.

Using the method described, it is possible to receive data from a mobile terminal unit continuously and with high quality without using a central processor, and at the same time to return to a short-range radio technology whenever possible. Such a preference for short-range radio technology has the advantage that the load on the long-range radio network is reduced. Further, it minimizes power consumption, as the transmitted radio signal only needs to have a short range. The latter fact particularly benefits mobile devices which are to be powered by batteries with limited capacity. Provided that the original radio link is maintained for at least the time required to establish a new link when handing over, the method ensures loss-free data transmission.

The quality of the communication link via the short-range radio technology can in particular be determined on the basis of the signal strength, error rate and/or the noise level (signal-to-noise ratio) of this link. They are expressive parameters for the stability and quality of a communication link.

The short-range radio technology can in particular be based on the Bluetooth protocol. Bluetooth constitutes a widely used standard for wireless communication between data processing devices over short ranges, i.e. a range of about ten meters.

Preferably, the long-range radio technology is preferably based on a standard for wireless local area networks (WLANs). Particular examples are the IEEE802.11 or DECT standards.

The terminal unit can optionally be provided with sensors which allow measurement of physiological parameters such as the ECG of a patient. In this case, the method can particularly be used to monitor a patient.

In a further feature of the invention, communication occurs via the different radio technologies with stations of the receiving system which are spaced apart. In particular, communication via the long-range radio technology can take place with a central processor, while different local stations can be made available as communication partners for the short-range radio technology.

In a further feature of the method, the transmitted data streams are synchronized on switching between two radio technologies. Differences in delay, which may occur when different transmission routes are used, are thus canceled, so that a continuous, synchronous data stream arrives at the receiving system.

The invention also concerns a patient monitoring system for the mobile acquisition of physiological data from a patient. The patient monitoring system contains a mobile terminal unit with sensors for measuring the desired physiological parameters and a receiving system, to which the data measured by the terminal unit are transmitted. The terminal unit and the receiving system are arranged so that they can carry out a method of the type described above. This means that the terminal unit can transmit data to the receiving system via short-range and long-range radio technology. The short-range radio technology is then preferably employed, i.e. whenever a communication link of sufficient quality makes it possible. Automatic switching between the radio technologies has the advantage that it requires no input from medical personnel if, for example, a patient wishes to get up out of bed and move around. Preferring the short-range radio technology also minimizes power consumption and thus optimizes battery life in the mobile terminal unit. At the same time, the network of the long-range radio technology is freed from local data transmission.

In a preferred implementation, the patient monitoring system comprises (at least) a first station with which the terminal unit can communicate via short-range radio technology, and a second station with which the terminal unit can communicate via long-range radio technology. Typically, the second station is located at a central spot in a clinic, while stations of the first type are local, meaning in particular arranged in every ward or by every patient's bed.

Preferably, said first and second stations are networked (wire-bound or wireless) so that all of the data acquired by them can be further processed centrally.

These and other aspects of the invention are apparent from and will be elucidated by way of non limiting example with reference to the Figure. The sole Figure diagrammatically shows a special use of the invention in the context of a patient monitoring system.

The patient monitoring system of the invention allows continuous acquisition of vital parameters such as the ECG of a hospital patient. Generally, the patient being monitored is stationary in bed. However, monitoring should be able to be continued without a break if the patient occasionally moves around the ward or within the hospital.

To acquire the desired data from the patient, a mobile terminal unit 1 carried by the patient is provided. As long as the patient is in his ward, the terminal unit 1 continuously transfers the measured data to a local data monitor 3 at the patient's bed using a short-range radio technology such as a Bluetooth link 2. The distance to be covered is only a few meters. The radio signals thus only need to have a short range, thus minimizing the power consumption on the terminal unit 1.

If the patient leaves the room, the short-range radio technology 2 is no longer suitable for data transmission. In this case, the terminal unit 1 according to the invention automatically switches to long-range radio technology 7. This may in particular be a known technology of wireless local area networks (WLAN), via which data can be transmitted from terminal unit 1 to an antenna 6. Examples of suitable long-range radio technologies are the IEEE802.11 and DECT standards.

As soon as the patient returns to within the range of the short-range radio technology 2, the communication is switched again to minimize the power consumption of the terminal unit 1 and as far as possible to relieve the load on the long-range wireless network as much as possible.

The transition between the short-range radio technology 2 and the long-range radio technology 7 then preferably takes place when the quality of the short-range link 2, which is determined by parameters such as the error rate, signal strength and/or signal-to-noise ratio, for example, surpasses predetermined thresholds. The threshold for a transition from short range to long range is then preferably set so high that the transition to the long-range radio technology occurs while the short-range link still has a certain stability reserve. In this manner, a safe transmission can be guaranteed without data loss, which is critical when switching from short range to long range because in this case, there is a threat of a breakdown of the short-range link.

Furthermore, a transition-free handover between two radio technologies without data loss is guaranteed in that one link (e.g. the Bluetooth link 2) is only terminated when the new link 7 is fully established.

Preferably, the data streams transmitted via the various radio technologies are synchronized in order to cancel different transit delays arising from different transmission routes. For the very different transmission routes, the delays for the two routes will generally vary to a greater or lesser extent. When switching a real-time data stream from one transmission route to another, care should be taken that the data are time synchronized. Alternatively, when switching from a short delay to a longer delay, there will be a gap, and when switching from a long to a shorter delay, newer data can arrive in the central processor before older data. Synchronization can be effected for example by using time stamps in the transmitted data, using sequence numbers of the transmitted data packets, or using a receiving buffer that has the size of the maximum allowable delay. Time delay variations can be intercepted by the receiving buffer, and sequence numbers and time stamps prevent the received data from getting into the wrong order.

The Figure also shows that the stations for receiving the short-range radio signals and the long-range radio signals are separated physically and spatially. As already mentioned, the short-range radio signals 2 are primarily directed to a data monitor arranged by the patient's bed. The long-range radio signals, however, can be received by a central antenna 6 which is connected to a server 5. Further, server 5 is further preferably connected to the various data monitors 3 at the patient's bedside via a wire-bound local area network 4. This means that there is a WLAN infrastructure (wireless local area network: 30 m-100 m), which comprises a plurality of access points which are directly connected via a wire-bound network 4 to the central processor 5. Further, medical devices (such as the patient's monitors 3) are also connected to the same network (preferably wire-bound, but also wireless via a WLAN infrastructure). The terminal unit 1 can now communicate with the central processor 5 via two separate routes: directly via the WLAN infrastructure, or indirectly via a short-range radio technology via the patient monitor 3 as a relay station.

When handing over between the short-range and long-range radio technologies, the peculiarity exists that two very different transmission systems are being switched between. One is a short-range transmission system, in which a medical device 3 represents the transformation into a monitoring network, and the other is a long-range transmission system with direct access to the monitoring network.

The flexible usage described above of two radio technologies can clearly be employed in the context of monitoring patients, but also with other wireless display devices for audio or video data, which can switch between various radio technologies as and when required.

LIST OF REFERENCE NUMBERS

Mobile terminal unit;
Short-range radio technology;
Data monitor;
Network cabling;
Server;
Antenna
Long-range radio technology.

The invention claimed is:

1. A method of controlling wireless data transmission from a mobile terminal unit to a receiving system, wherein:
   a) the terminal unit transmits data to a network via a short-range radio technology in a first mode and monitors quality of the communication link and automatically switches to a second mode in response to the quality of the communication link via the short-range radio technology falling below a first predetermined threshold;
   b) the terminal unit transmits data to the network via a long-range radio technology while monitoring the quality of the communication link via the first mode and automatically switches to the first mode as soon as the quality of the communication link via the short-range radio technology is above a second predetermined threshold;

c) on switching from one mode to the other, the communication link via the radio technology of the previous mode is maintained until the link is established via the radio technology of the subsequent mode.

2. A method according to claim 1, wherein the quality of the communication link via the short-range radio technology is determined by the signal strength, the error rate and/or the signal to noise distance of the communication link.

3. A method according to claim 1, wherein the short-range radio technology is based on the Bluetooth protocol.

4. A method according to claim 1, wherein the long-range radio technology is based on a WLAN standard.

5. A method according to claim 1, wherein the communication via the short range radio technology is carried out using stations of the receiving system that are spatially separated from stations of the long range radio technology.

6. A method according to claim 1, wherein when switching between two radio technologies, the transmitted data streams are synchronized.

7. A patient monitoring system for mobile acquisition of a patient's physiological parameters, comprising a mobile terminal unit and a receiving system, which is arranged to carry out a method according to claim 1.

8. A patient monitoring system according to claim 7, wherein the receiving system comprises a first station with which the terminal unit can communicate via the short-range radio technology, and a second station with which the terminal unit can communicate via the long-range radio technology.

9. A patient monitoring system according to claim 8, wherein the first and second stations are networked.

10. A method of controlling wireless data transmission from a mobile terminal unit to a receiving system, wherein:

a) the terminal unit transmits data to a network via a shod-range radio technology in a first mode and monitors quality of the communication link and automatically switches to a second mode in response to the quality of the communication link via the short-range radio technology falling below a first predetermined threshold, the terminal unit having sensors for measuring physiological parameters of a patient;

b) the terminal unit transmits data to the network via a long-range radio technology while monitoring the quality of the communication link via the first mode and automatically switches to the first mode as soon as the quality of the communication link via the short-range radio technology is above a second predetermined threshold;

c) on switching from one mode to the other, the communication link via the radio technology of the previous mode is maintained until the link is established via the radio technology of the subsequent mode.

11. A patient monitoring system for mobile acquisition of a patient's physiological parameters, comprising:

at least one mobile terminal unit which acquires the patient's physiological parameters, the mobile terminal unit being configured to:

transmit physiological parameter data to a network via a short range radio technology in a first mode while monitoring a quality of a communication link via the short range radio technology, and switch to a second mode in response to the quality of the communication link via the short range radio technology falling below a first predetermined threshold, and transmit the physiological parameter data via a long range radio technology in the second mode while monitoring the quality of the communication link via the short range radio technology and switch automatically back to the first mode as soon as the quality of the communication link via the short range radio technology is above a second predetermined threshold, and maintain the communication link via the short range radio technology until the communication link is established via the long range radio technology when switching from the first mode to the second mode, and maintain the communication link established via the long range radio technology until the communication link is established via the short range radio technology when switching from the second mode to the first mode, such that at least one communication link is always maintained; and a receiving system which receives the physiological parameter data from the at least one mobile terminal unit, the receiving system including:

a first station which communicates via the at least one mobile terminal unit via the short range radio technology, and a second station which communicates with the at least one mobile terminal unit via the long range radio technology.

* * * * *